(12) United States Patent
Zhao et al.

(10) Patent No.: US 11,090,022 B2
(45) Date of Patent: Aug. 17, 2021

(54) DYNAMIC TEST PHANTOM SIMULATING CARDIOVASCULAR MOTION FOR QUALITY EVALUATION OF CT IMAGING, AND ITS CONTROL PRINCIPLE AND QUALITY TESTING METHOD

(71) Applicant: THE SECOND AFFILIATED HOSPITAL OF PLA ARMY MEDICAL UNIVERSITY, Chongqing (CN)

(72) Inventors: Peng Zhao, Chongqing (CN); YinBao Chong, Chongqing (CN); WenCai Pan, Chongqing (CN); Lang Lang, Chongqing (CN); Jiaqing Yang, Chongqing (CN); Jingjing Xiao, Chongqing (CN); Jieshi Ma, Chongqing (CN); ShiHui Zhang, Chongqing (CN)

(73) Assignee: THE SECOND AFFILIATED HOSPITAL OF PLA ARMY MEDICAL UNIVERSITY, Chongqing (CN)

( * ) Notice: Subject to any disclaimer, the term of this patent is extended or adjusted under 35 U.S.C. 154(b) by 3 days.

(21) Appl. No.: 16/754,375

(22) PCT Filed: Jan. 10, 2019

(86) PCT No.: PCT/CN2019/071231
§ 371 (c)(1),
(2) Date: Apr. 8, 2020

(87) PCT Pub. No.: WO2020/140302
PCT Pub. Date: Jul. 9, 2020

(65) Prior Publication Data
US 2021/0212654 A1 Jul. 15, 2021

(30) Foreign Application Priority Data

Jan. 4, 2019 (CN) .......................... 201910008685.7

(51) Int. Cl.
*A61B 6/00* (2006.01)
*A61B 6/03* (2006.01)

(52) U.S. Cl.
CPC .............. *A61B 6/583* (2013.01); *A61B 6/032* (2013.01); *A61B 6/503* (2013.01)

(58) Field of Classification Search
CPC ............ A61B 6/583; A61B 2034/2048; A61B 2090/372; A61B 5/055; A61B 6/542;
(Continued)

(56) References Cited

U.S. PATENT DOCUMENTS

| 2003/0045803 | A1* | 3/2003 | Acharya | A61B 6/032 600/508 |
| 2006/0027741 | A1* | 2/2006 | Faber | G09B 23/28 250/252.1 |
| 2014/0069215 | A1* | 3/2014 | Tavakoli | A61B 5/055 73/866.4 |

FOREIGN PATENT DOCUMENTS

| CN | 205338954 | 6/2016 |
| CN | 106463067 | 2/2017 |

OTHER PUBLICATIONS

"International Search Report (Form PCT/ISA/210) of PCT/CN2019/071231," dated Sep. 19, 2019, pp. 1-4.

* cited by examiner

*Primary Examiner* — Courtney D Thomas
(74) *Attorney, Agent, or Firm* — JCIP Global Inc.

(57) ABSTRACT

The invention discloses a quality testing method dynamic test phantom simulating cardiovascular motion for quality
(Continued)

evaluation of CT imaging, and its control principle and quality testing method. The dynamic test phantom includes: a control system, an electric cylinder unit, a piston pump unit, a fluid circuit unit and a cardiovascular phantom; the control system includes a control box and a control PC, wherein the control box includes a PLC control system and an electrocardiogram generator, and the PLC control system is connected with the control PC and the electrocardiogram generator respectively; the electric cylinder unit includes an electric cylinder drive unit and an electric cylinder transmission unit, wherein the electric cylinder drive unit is connected with the PLC control system, and the electric cylinder transmission unit is connected with the electric cylinder drive unit; the piston pump unit is connected with the electric cylinder transmission unit; the fluid circuit unit includes a fluid confluence module and fluid pipelines, which are connected with the piston pump unit and the cardiovascular phantom respectively; and the cardiovascular phantom includes a ventricular phantom, coronary artery phantoms and a water tank. The dynamic test phantom according to the invention can simulate ventricular strokes and multiple motion phases, and has standard models of normal heart rate, arrhythmis, coronary artery stenosis, etc.

10 Claims, 12 Drawing Sheets

(58) Field of Classification Search
CPC ....... A61B 6/488; A61B 6/503; G06T 7/0012; G06T 2207/10081
See application file for complete search history.

DYNAMIC TEST PHANTOM SIMULATING CARDIOVASCULAR MOTION FOR QUALITY EVALUATION OF CT IMAGING, AND ITS CONTROL PRINCIPLE AND QUALITY TESTING METHOD

CROSS-REFERENCE TO RELATED APPLICATION

This application is a 371 of international application of PCT application serial no. PCT/CN2019/071231, filed on Jan. 10, 2019, which claims the priority benefit of China application no. 201910008685.7, filed on Jan. 4, 2019. The entirety of each of the above mentioned patent applications is hereby incorporated by reference herein and made a part of this specification.

BACKGROUND OF THE INVENTION

Technical Field

The invention belongs to the field of standardization technology for quality control of digital medical equipment, and in particular relates to a dynamic test phantom simulating cardiovascular motion for quality evaluation of CT imaging, and its control principle and quality testing method.

Description of Related Art

As a non-invasive imaging modality, computed tomography (CT) imaging has an accuracy of more than 80% in the diagnosis of cardiovascular diseases, and has gradually become an important examination method for early screening and postoperative evaluation. However, for the heart, which is the most complicated moving organ of a human body, cardiac CT imaging technologies in the prior art are susceptible to the differences in the heart rate of a patient, the performance of a CT device, the setting of scanning parameters, post-processing reconstruction and the like, resulting in problems such as motion artifacts, vascular transposition and edge blurring, which greatly reduces the cardiac CT imaging quality, seriously affects the accuracy in the diagnosis of cardiovascular diseases, and even worse, leads to disputes between doctors and patients. Therefore, how to guarantee the quality of the cardiac CT imaging is critical for the accurate diagnosis and treatment of cardiovascular diseases and the medical quality and safety.

At present, the specification of quality control for CT have developed in accordance with IEC 1223-2-6. The testing instruments are static phantoms such as head dose phantoms and image performance phantoms; and the testing items include CT dose index, slice thickness, CT value linearity, spatial resolution, low contrast resolution, CT value of water, field uniformity, noise, etc. The performance indicators above are based on the geometric projection principle or variations of an object under X ray attenuation, and are obtained through axial scanning. These performance indicators can be used in the objective evaluation of the static organ imaging quality of the CT device, but cannot be used in the imaging quality control of moving organs such as the cardiovascular system, especially during high-speed irregular motions such as tachycardia, premature beats, and atrial fibrillation. In other words, there is still a lack of a standard dynamic phantom as a testing instrument in the existing CT quality control system. In recent years, domestic and foreign scholars have reported numerous dynamic heart phantoms for simulating a cardiac anatomical structure and motion characteristics, and also for evaluating and studying different scanning methods and reconstruction algorithms for cardiac CT imaging. However, there are still numerous shortcomings of the existing dynamic heart phantoms, which are mainly in the following aspects: (1) regarding the anatomical structure, the liquid filled in most of the coronary artery phantoms cannot flow; (2) regarding the tissue material, composites such as silica gel or polyvinyl alcohol which have certain biomechanical properties are mainly used, but the radiation equivalence is not taken into consideration; and (3) regarding the motion characteristics, the motion of the atriums and ventricles is simulated only at constant speed or in a sinusoidal or simple speed-changing manner, and the real changes in the motion of the heart in each time phase are not reflected.

Therefore, it is necessary to develop a dynamic test phantom simulating cardiovascular motion for quality evaluation of CT imaging, and its control principle and quality testing method.

BRIEF SUMMARY OF THE INVENTION

An object of the invention is to provide a dynamic test phantom simulating cardiovascular motion for quality evaluation of CT imaging, and its control principle and quality testing method. The dynamic test phantom is capable of simulating ventricular strokes and five time-phase actions including rapid ejection, slow ejection, rapid filling, slow filling, and isovolumetric relaxation, have standard models of normal heart rate, arrhythmia, coronary artery stenosis, etc. and can be used in the quality testing of the cardiac CT imaging.

The dynamic test phantom simulating cardiovascular motion for quality evaluation of CT imaging according to the invention includes: a control system, an electric cylinder unit, a piston pump unit, a fluid circuit unit and a cardiovascular phantom, wherein the control system includes a control box and a control PC, wherein the control box includes a PLC control system and an electrocardiogram (ECG) generator, and the PLC control system is electrically connected with the control PC and the ECG generator respectively;

the electric cylinder unit includes an electric cylinder drive unit and an electric cylinder transmission unit, wherein the electric cylinder drive unit is connected with the PLC control system and the electric cylinder transmission unit respectively;

the piston pump unit is connected with the electric cylinder transmission unit, and the electric cylinder unit controls the piston pump unit to linearly reciprocate based on a command issued by the PLC control system, to pump a liquid in or out of the cardiovascular phantom through the fluid circuit unit;

the cardiovascular phantom includes a water tank, a ventricular phantom and coronary artery phantoms, wherein the ventricular phantom and the coronary artery phantoms are disposed in the water tank, the water tank is filled with the liquid, and the coronary artery phantoms include a plurality of catheters, each of which is in communication with the ventricular phantom respectively; and the fluid circuit unit includes a fluid confluence module and fluid pipelines, wherein the fluid pipelines include a pump-in fluid pipeline and pump-out fluid pipelines; the fluid confluence module includes a fluid flow sensor and a diverter block; the fluid flow sensor is electrically connected with the PLC control system and is installed between the piston pump unit and the diverter block; the diverter block is internally provided with a pump-in check valve and a pump-out check valve; the pump-in check valve has a water inlet end in communication with the fluid flow sensor and has a water outlet end in communication with the ventricular phantom through the pump-in fluid pipeline; the pump-out check valve has a water outlet end in communication with the fluid flow sensor and has a water inlet end respectively in communication with one end of each of the pump-out fluid pipelines; and the other ends of the plurality of pump-out fluid pipelines are in one-to-one correspondence with the plurality of catheters respectively.

Further, the fluid circuit unit further includes a buffer, the bottom of the buffer is in communication with the diverter block through a buffer interface, and the top of the buffer is provided with a water injection valve, a gas pressure gauge and a vent hole.

Further, the ventricular phantom is made of silica gel, and has an elliptical shape with openings at both ends.

Further, the coronary artery phantoms are synthesized from a high polymer material of a polytetrahydrofuran ether polyol-toluene diisocyanate copolymer, with a CT value ranging from 30HU-80HU.

Further, the coronary artery phantoms are classified into a normal coronary artery phantom and coronary artery phantoms having different levels of stenosis; each catheter of the normal coronary artery phantom has the same inner diameter; and each catheter of the coronary artery phantom having different levels of stenosis has simulated calcified plaques or soft plaques in the lumen to lead to the stenosis levels of 25%, 50% and 75%.

Further, the PLC control system includes a CPU module, a motion control module, two communication modules, and a power module; the CPU module is connected with the motion control module, two communication modules and the power module respectively; the motion control module is connected with the electric cylinder unit; one of the communication modules is connected with the control PC; and the other communication module is connected with the ECG generator.

Further, the electric cylinder transmission unit includes a motor and a transmission construct which converts the rotation of the motor into a linear motion.

The transmission construct includes a synchronous belt, a synchronous wheel, a ball screw, a screw nut, a cylinder body and a push rod; the motor is connected with the ball screw through the synchronous belt and the synchronous wheel; the screw nut is connected with the push rod; the push rod is located in the cylinder body; the motor is transmitted to the ball screw through the synchronous wheel and the synchronous belt; and the ball screw drives the screw nut to convert the rotation into the linear motion, so that the push rod reciprocates linearly along the cylinder body.

Further, the water inlet end of the ventricular phantom is connected with the pump-in fluid pipeline through a pump-in pipe interface; and the water outlet end of the ventricular phantom is in communication with each of the catheters of the coronary artery phantom through a three-way connector, which is provided with a drain valve.

A method for controlling a dynamic test phantom simulating cardiovascular motion for quality evaluation of CT imaging according to the invention employs the dynamic test phantom simulating cardiovascular motion for quality evaluation of CT imaging as described in the invention, and the method includes the following steps:

acquiring ventricular motion parameters, converting the ventricular motion parameters into motion control variables, and storing the motion control variables, by a control PC, wherein the ventricular motion parameters include a heart rate and a ventricular volume-time curve, the motion control variables include a motion cycle, each motion phase and its flow value; when starting control, sending a start-up instruction to the PLC control system, and displaying and storing an ECG waveform, the ventricular volume-time curve, the heart rate, a cardiac cycle, and a stroke volume in real time;

receiving a command sent from the control PC by the PLC control system; if the command is the start-up instruction, parsing the motion control variables in the start-up instruction, calculating the flow of the piston pump unit in unit time using a closed-loop control algorithm, calculating motion control parameters based on displacements fed back in real time, sending a motion control signal to the electric cylinder drive unit while sending an ECG control command to the ECG generator to output an ECG waveform, and after waiting for the action to be completed, sending a stop instruction to the electric cylinder unit and the ECG generator respectively; and if the command is the stop instruction, directly sending a stop instruction to the electric cylinder unit and the ECG generator after waiting for the current action to be completed, and automatically returning to zero; then, continuing to monitor if a command from the control PC is received; and repeating the process above again and again till the end of a run.

A CT imaging quality testing method according to the invention employs the dynamic test phantom simulating cardiovascular motion for quality evaluation of CT imaging as described in the invention, and the method includes the following steps:

Step 1, establishment of a connection, to be specific, placing the control system, the electric cylinder unit, the piston pump unit, the fluid circuit unit and the cardiovascular phantom on a scanning bed of a CT device, and performing installation and connection;

Step 2, establishment of a fluid circuit, to be specific, opening the water injection valve and the vent hole of the buffer, injecting a target solution prepared by mixing distilled water and a contrast agent into the piston pump unit and the ventricular phantom, removing air, closing the water injection valve after completing the injection, installing the gas pressure gauge to the vent hole and tightening, and then injecting the distilled water into the water tank to act as a background solution;

Step 3, power-on for startup, to be specific, turning on the power switch of the control box, and starting the control PC;

Step 4, removal of air, to be specific, opening application software of the control PC, setting the heart rate and the ventricular volume-time curve, starting a motion, running till air in the fluid circuit are removed and air at the top of the buffer is compressed and then maintained at a preset pressure value, and stopping the motion; or else, checking the tightness of each pipeline and its interface, and repeating the process above;

Step 5, starting of control, to be specific, setting the motion parameters through the application software of the control PC, sending a motion control command to the PLC control system, which controls the piston pump unit to reciprocate linearly to pump a liquid out of or in the cardiovascular phantom for simulating ventricular strokes and multiple motion time phases, and simultaneously sending an ECG signal to trigger ECG-gated scanning of the CT device;

Step 6, image acquisition, to be specific, positioning the cardiovascular phantom, creating a new patient, selecting a CTA examination protocol, setting scanning conditions, and scanning the cardiovascular phantom; and Step 7, clinical evaluation, to be specific, performing post-processing and 3D reconstruction using clinical application software of the CT device to obtain relevant evaluation indexes of the cardiovascular phantom, and evaluating imaging quality of the CT device.

The invention has the following advantages:

(1) the CT values of both the coronary artery phantoms and the ventricular phantom are equivalent to those of human tissues;

(2) the coronary artery phantom has different levels of stenosis;

(3) the heart rate and the time-volume curve (a custom curve for at least 20 points) can be set;

(4) the ventricular beats can be simulated with multiple motion phases;

(5) the arrhythmia, coronary stenosis and other common lesion models of a real patient can be simulated; and (6) the invention is applicable to the study on the evaluation of the CT device and its clinical application software.

DETAILED DESCRIPTION OF THE INVENTION

The invention will be further described below with reference to the accompanying drawings.

Figure 1:
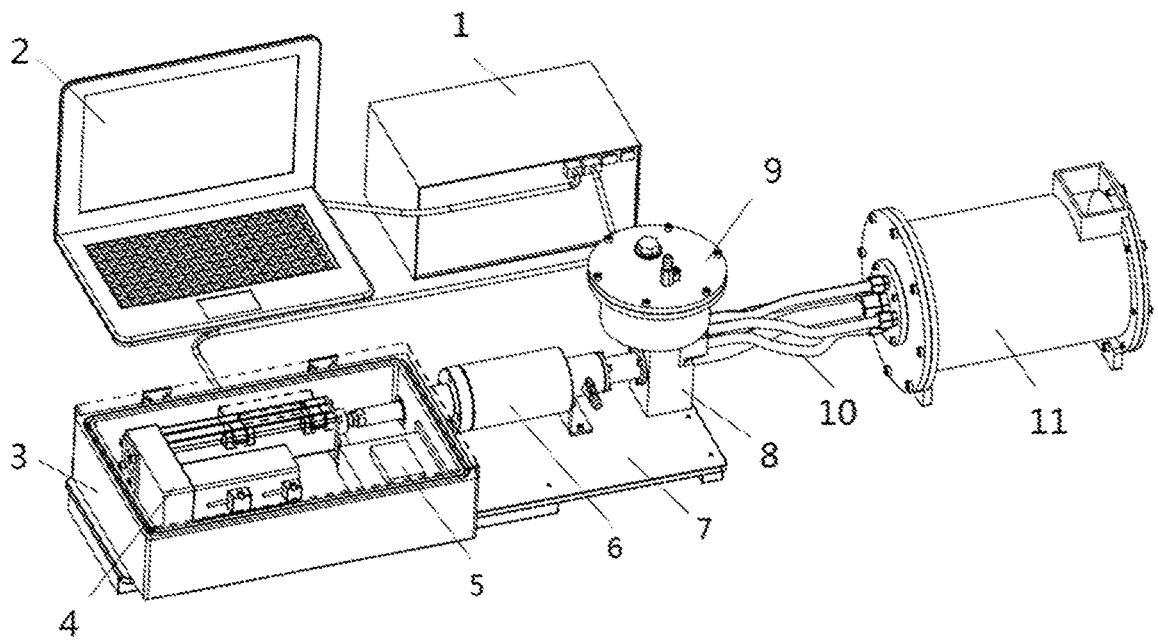
FIG. 1 is a schematic diagram of a structure according to the invention.
Figure 2:
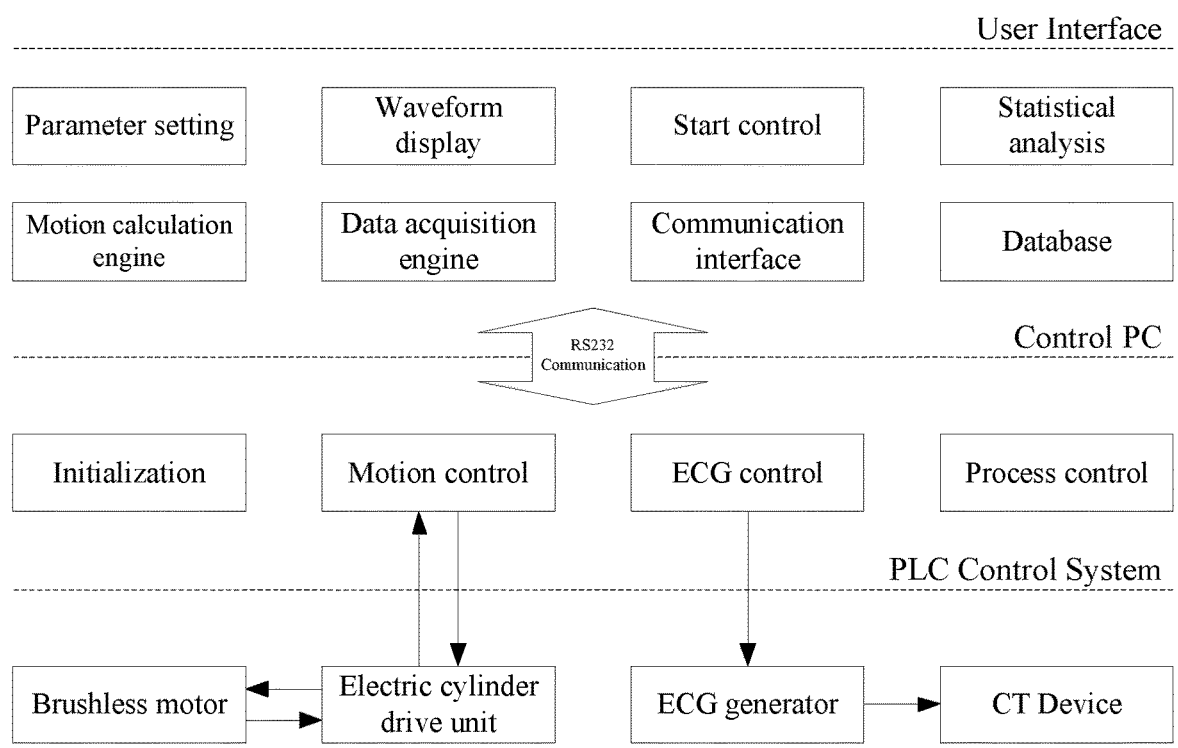
FIG. 2 is a block diagram showing the principle of the invention.

(1) Structure and Composition of the Phantom:

As shown in FIG. 1 and FIG. 2, the dynamic test phantom simulating cardiovascular motion for quality evaluation of CT imaging in this embodiment includes: a control system, an electric cylinder unit 3, a piston pump unit 6, a fluid circuit unit and a cardiovascular phantom 11.

Control System:

As shown in FIG. 1, in this embodiment, the control system includes a control box 1 and a control PC 2.

The control box 1 includes a PLC control system and an ECG generator; the control box 1 is provided with an RS232 interface, a DB18 interface, an ECG interface, a single-phase power interface and a power switch; and the control PC 2 and the electric cylinder unit 3 are supplied with working power respectively through the single-phase power interface and the power line.

The PLC control system consists of a CPU module, a motion control module, two communication modules (for example, RS232 communication modules) and a power module, wherein the motion control module is connected with the fluid flow sensor through the DB18 interface, the data line and the electric cylinder unit 3 respectively, to send motion control commands and receive electric cylinder displacement data and flow feedback data; one of the RS232 communication modules is connected with the control PC 2 through a serial port line for communication with the control PC 2; the other communication module is connected with the ECG generator through a RS232-to-USB data line for transmitting a preset heart rate parameter; the power module is configured to convert the AC 220V into DC 24V for supplying the PLC control system with the operating power; and the ECG generator is connected with a CT ECG acquisition apparatus or a CT device through the ECG interface and the ECG cable for ECG-gated scanning.

As shown in FIG. 2, in this embodiment, the control PC 2 is internally installed with the application software, which is divided into an application layer, an intermediate layer and a data layer, wherein the application layer includes four functional modules involving parameter setting, waveform display, startup control, and statistical analysis, for providing users with a human-computer interaction interface, and displaying an ECG waveform, a ventricular volume-time curve, a heart rate, a cardiac cycle and a stroke volume and other values in real time during the running of the system; the intermediate layer includes a motion calculation engine, a data acquisition and storage engine and a communication interface; the motion calculation engine is configured to convert the preset values of the heart rate and the ventricular volume time curve into motion control variable parameters, including the motion cycle, each motion time phase and flow value, and package the data and send the packaged data to the PCL control system; the data acquisition and storage engine is configured to collect and store data such as the motion control variable parameters and the real-time waveforms; and the communication interface is configured to perform data communication with the PCL control system through the serial port protocol.

The PLC control system is installed with the control software, and the control software includes four functional modules involving initialization, motion control, ECG control and flow control, wherein the initialization module is configured to initialize system parameters, the zeroing of the electric cylinder position, and the resetting of the ECG generator; the motion control module is configured to parse the motion control variable parameters sent by the control PC 2, calculate the motion control parameters by using a closed-loop control algorithm (for example, a PID controller) and real-time feedback (for example, displacement and flow) and send the motion control parameters to the electric cylinder drive unit 5, so that the electric cylinder transmission unit 4 moves according to the command; the ECG control module is configured to, in synchronization with the motion control command, send an ECG control command to the ECG generator for outputting an ECG waveform; and the flow control module is configured to perform process management on the PLC program in a code memory during runtime, so as to increase the system response speed and the reliability.

Electric Cylinder Unit:

As shown in FIG. 1, in this embodiment, the electric cylinder unit 3 includes an electric cylinder drive unit 5 and an electric cylinder transmission unit 4, and is provided with a DB15 interface and a via hole;

With the operating voltage of 220V and the rated power of 100 W, the electric cylinder drive unit 5 is connected with the PLC control system through the DB15 interface and a data line, and connected with the electric cylinder transmission unit 4 through a control signal line, and can convert the motion control parameters of the PLC control system into control signals required by the electric cylinder transmission unit 4, and convert the rotational speed and the rotation number of a motor into the displacements of the electric cylinder to be fed back to the PLC control system;

The electric transmission construct 4 includes a synchronous belt, a synchronous wheel, a ball screw, a screw nut, a cylinder body and a push rod; the motor is connected with the ball screw through the synchronous belt and the synchronous wheel; the screw nut is connected with the push rod; and the push rod is located in the cylinder body. The motor has the rated power of 400 W, the maximum speed is 5000 RPM, and the maximum stroke of 100 mm; the motor rotates in a forward or reverse direction after receiving a control signal, and transmits the rotation to a ball screw through a synchronous wheel and a synchronous belt; the ball screw drives a screw nut to convert the rotation into a linear motion, to enable a push rod to reciprocate linearly; the motor is provided with a Hall sensor, which may feedback the rotation number of the motor in real time and send the rotation number to the electric cylinder drive unit 5; and the electric cylinder drive unit 5 converts the rotation number of the motor into rotation speed, and automatically adjusts the control signal to be output to the motor, thereby ensuring the rotation speed of the motor speed reaches an expected value.

Figure 3:
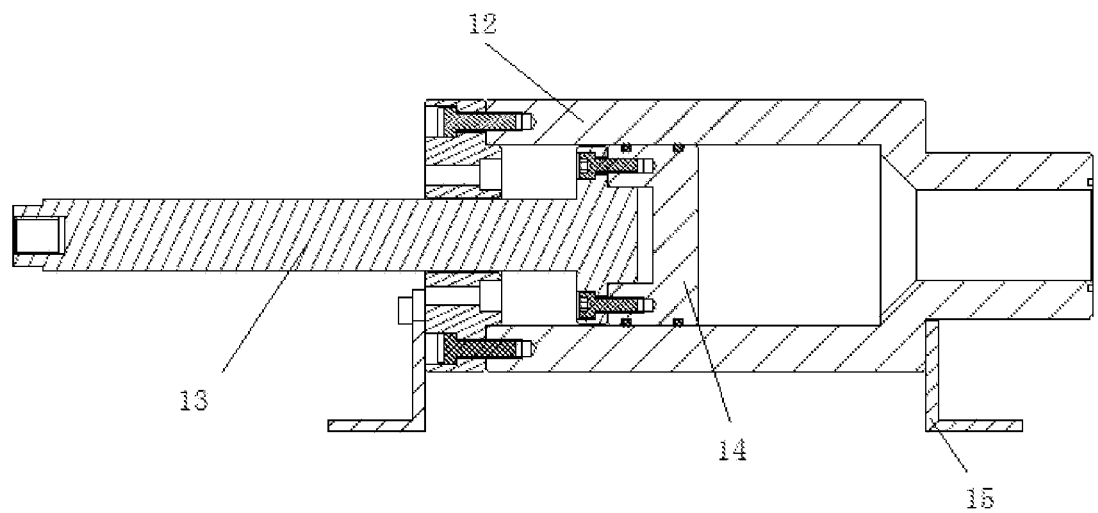
FIG. 3 is a schematic structural diagram of a piston pump unit according to the invention.

Piston Pump Unit:

As shown in FIG. 3, in this embodiment, the piston pump unit 6 includes a pump body 12, a piston 14, a connecting rod 13, star rings, and a support frame 15.

The pump body 12 is made of aluminum alloy with a cylindrical main body, and is fixedly installed on a support plate 7 through the support frame 15. A drain valve 31 is disposed outside the pump body 12 for draining all the liquid in the fluid circuit; the piston 14 is disposed inside the pump body 12 and is provided with two star rings for sealing a medium in the pump body 12, and meanwhile, one end of the piston 14 is fixedly connected with the connecting rod 13; and the connecting rod 13 is in threaded connection with the push rod of the electric cylinder transmission unit 4 through the via hole of the electric cylinder unit 3, and is driven by the push rod to reciprocate with the piston 14, thereby pumping the liquid in or out of the cardiovascular phantom 11 through the fluid circuit unit.

Figure 4:
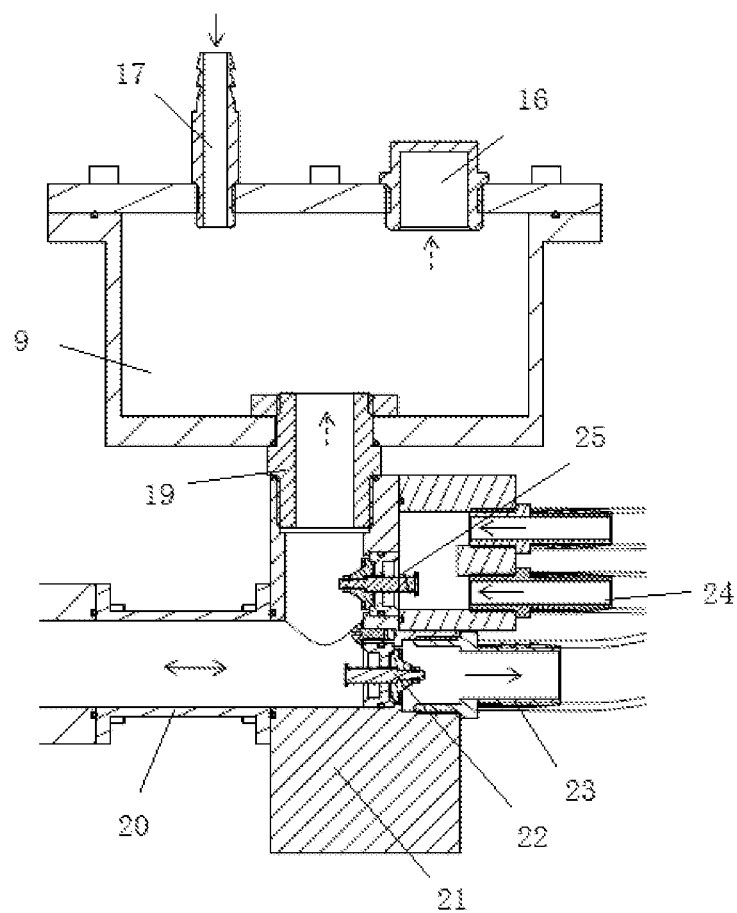
FIG. 4 is a schematic structural diagram of a fluid circuit unit according to the invention.

Fluid Circuit Unit:

As shown in FIG. 4, in this embodiment, the fluid circuit unit includes a fluid confluence module 8, a buffer 9 and fluid pipelines 10.

The fluid confluence module 8 includes a fluid flow sensor 20, a diverter block 21, a pump-in check valve 22, a pump-in pipe interface 23, a pump-out check valve 25, a pump-out pipe interface 24, and a buffer interface 19.

The fluid flow sensor 20 may output a pulse signal at a frequency that is in direct proportion to the flow of the measured fluid; the fluid flow sensor 20 is installed between the piston pump unit 6 and the diverter block 21 through a NPT 0.75 threaded interface for detecting the flow of the fluid pumped into the ventricular phantom 18 and the flow of the fluid flowing back from the coronary artery phantom 26 in real time, and sending the flow to the PLC control system through the data line in real time. The diverter block 21 is made of organic glass, and is internally provided with the pump-in check valve 22 and the pump-out check valve 25. The diverter block 21 is connected with the piston pump unit 6 at one side through the fluid flow sensor 20, and at the other side, is connected with the pump-in fluid pipeline through the pump-in pipe interface 23 via the pump-in check valve 22 and with the pump-out fluid pipelines through the pump-out pipe interfaces 24 via the pump-out check valve 25, respectively; the diverter block 21 is connected with the buffer 9 at the top through the buffer interface 19, and fixed on the support plate 7 at the bottom; and the number of the pump-out pipe interfaces 24 is the same as that of the catheters in the coronary artery phantom 26, and is connected with the cardiovascular phantom 11 through the fluid pipelines 10 respectively.

The buffer 9 is a cylindrical organic glass can for injecting water and removing air in the fluid circuit; and the bottom of the buffer 9 is installed on the diverter block 21 through the buffer interface 19, and the top of the buffer 9 is fixed with a flange plate, a rubber ring and an aluminum countersink screw. The flange plate is provided with a water injection valve 17, a gas pressure gauge and a vent hole 16 respectively; the water injection valve 17 is configured to inject the liquid into the piston pump unit 6 and the ventricular phantom 18 through the buffer 9; if a liquid is injected (for example, a mixed solution of distilled water and a contrast agent), the vent hole 16 needs to be opened, and once the injection is completed, the gasp pressure gauge is installed on the vent hole 16 in a threaded manner and then tightly closed; the gas pressure gauge is configured to observe if air in the fluid circuit are removed and air at the top of the buffer 9 is compressed and then maintained at certain pressure value when the system is initialized.

The fluid pipelines 10 may be PVC hoses, with one for the connection of the ventricular phantom 18, and two or more for the connection of the coronary artery phantom 26.

Figure 5:
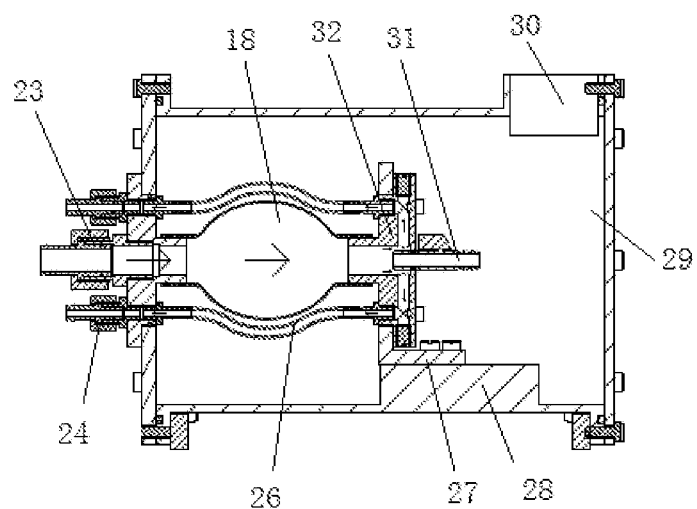
FIG. 5 is a schematic structural diagram of a cardiovascular phantom according to the invention.
Figure 6:
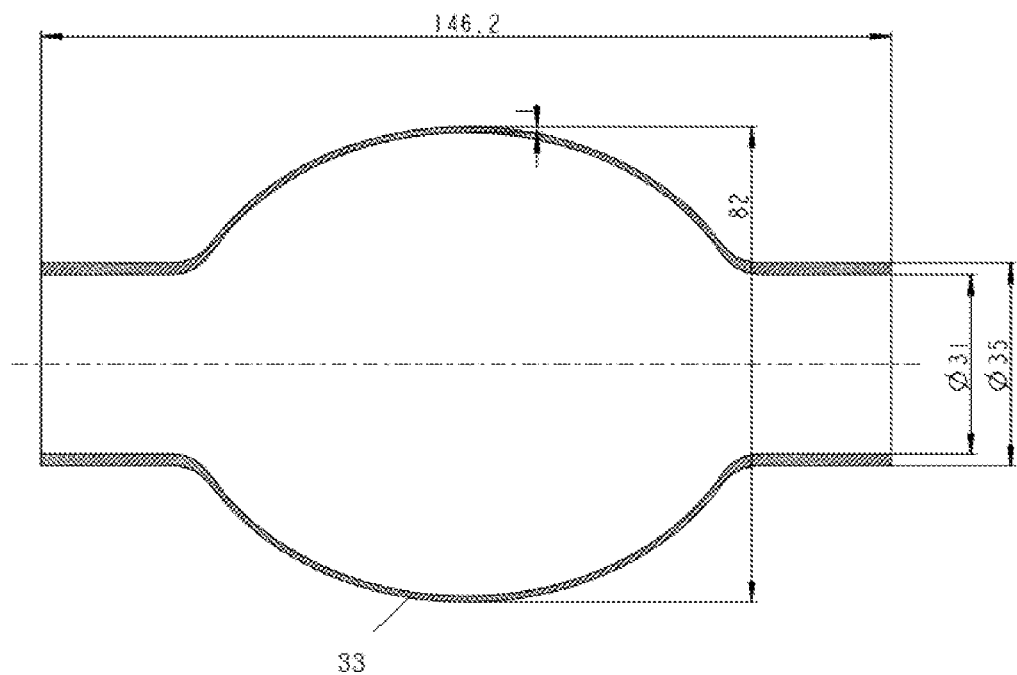
FIG. 6 is a dimensional diagram of a ventricular phantom balloon according to the invention.
Figure 7:
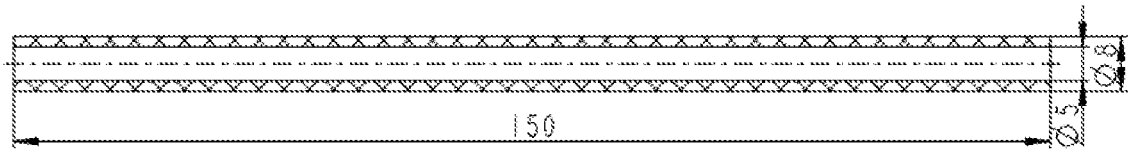
FIG. 7 is a dimensional diagram of a normal coronary artery phantom having an inner diameter of 5 mm according to the invention.
Figure 8:
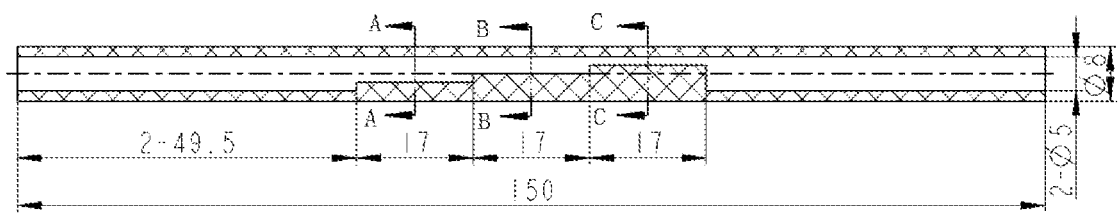
FIG. 8 is a dimensional diagram of a simulated coronary artery having an inner diameter of 5 mm for simulating different levels of stenosis.
Figure 9:
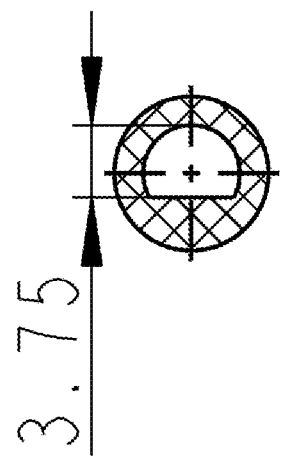
FIG. 9 is a sectional view along a line A-A in FIG. 8.
Figure 10:
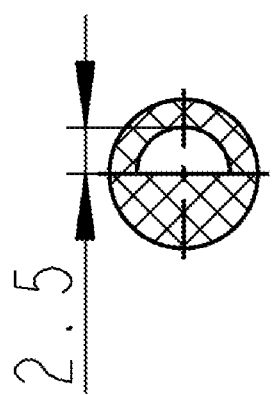
FIG. 10 is a sectional view along a line B-B in FIG. 8.
Figure 11:
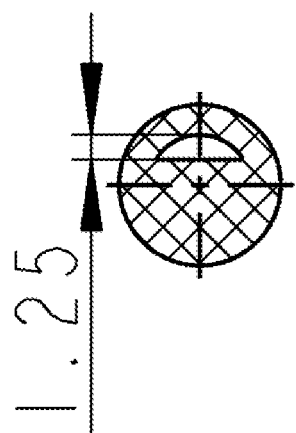
FIG. 11 is a sectional view along a line C-C in FIG. 8.
Figure 12:
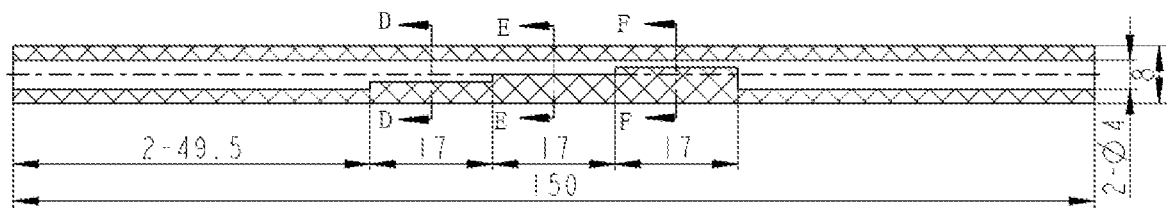
FIG. 12 is a dimensional diagram of a simulated coronary artery having an inner diameter of 4 mm for simulating different levels of stenosis.
Figure 13:
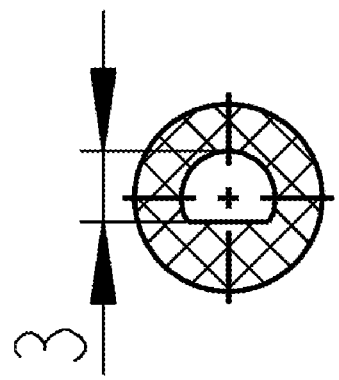
FIG. 13 is a sectional view along a line D-D in FIG. 12.
Figure 14:
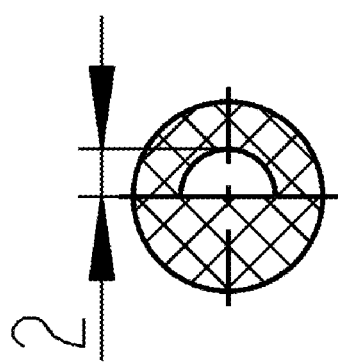
FIG. 14 is a sectional view along a line E-E in FIG. 12.
Figure 15:
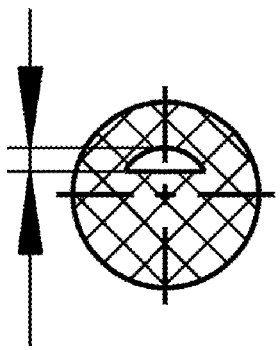
FIG. 15 is a sectional view along a line F-F in FIG. 12.
Figure 16:
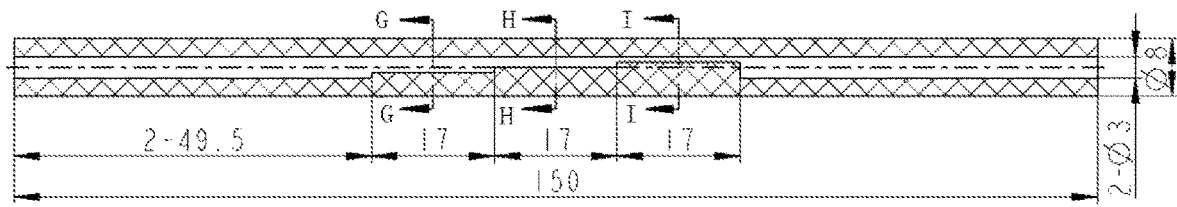
FIG. 16 is a dimensional diagram of a simulated coronary artery having an inner diameter of 3 mm for simulating different levels of stenosis.
Figure 17:
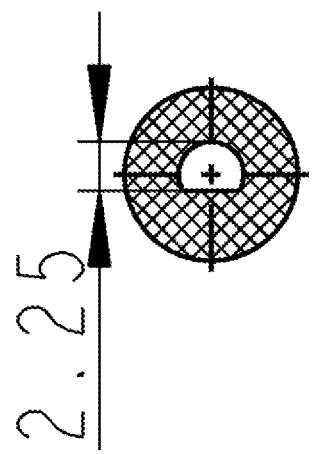
FIG. 17 is a sectional view along a line G-G in FIG. 16.
Figure 18:
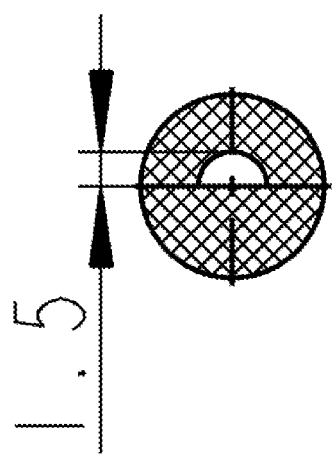
FIG. 18 is a sectional view along a line H-H in FIG. 16.
Figure 19:
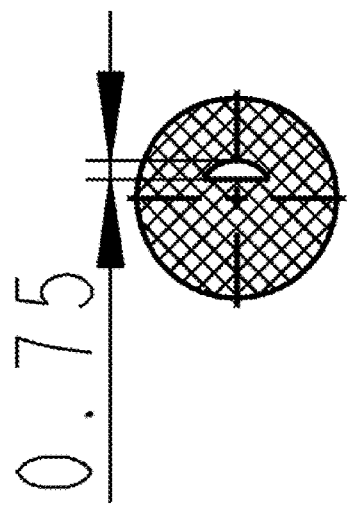
FIG. 19 is a sectional view along a line I-I in FIG. 16.

Cardiovascular Phantom:

As shown in FIG. 5, in this embodiment, the cardiovascular phantom 11 includes a ventricular phantom 18, a coronary artery phantom 26 and a water tank 29.

The ventricular phantom 18 is made of silica gel and has an elliptical shape, with openings at both ends and a certain elasticity; an inlet end of the ventricular phantom 18 is installed on the pump-in pipe interface 23 of the water tank 29; and an outlet end of the ventricular phantom 18 is installed on a three-way connector 32 on a base 28 inside the water tank 29.

The coronary artery phantoms 26 are synthesized from a high polymer material of a polytetrahydrofuran ether polyol-toluene diisocyanate copolymer, with a CT value ranging from 30HU-80HU; and each of the coronary artery phantom 26 includes two or more catheters having inner diameters of 3 mm, 4 mm, and 5 mm, respectively. As shown in FIG. 8 to FIG. 19, the coronary artery phantoms are classified into a normal coronary artery phantom 26 and a coronary artery phantom 26 having different levels of stenosis; the normal coronary artery phantom 26 has a cavity in which a coronary stent can be placed, and the coronary artery phantom 26 having different levels of stenosis has simulated calcified plaques or soft plaques in its lumen to lead to the stenosis levels of 25%, 50% and 75% (each with the length of 10 mm).

The water tank 29 is a cylindrical organic glass container which is filled with a background solution (for example, distilled water) and configured for the installation and fixation of the ventricular phantom 18 and the coronary artery phantoms 26; the top of the water tank 29 is provided with a window 30 for injecting water into the water tank 29 and preventing liquid overflow; both sides of the water tank 29 are fixed by the flange plates, the rubber rings and the aluminum countersink screws; the flange plate at one side has a center hole for the installation of a center disc, which is provided with the pump-in pipe interface 23 and the pump-out pipe interfaces 24; the pump-in pipe interface 23 at an inside end of the water tank 29 is used for the installation of the ventricular phantom 18, the pump-out pipe interfaces 24 at an outside end of the water tank 29 is used for the installation of the coronary artery phantom 26, and the pump-in pipe interface 23 and the pump-out pipe interface 24 at the outside end of the water tank 29 are used for the connection of the fluid pipelines 10; the water tank 29 is internally provided with a base 28 for the installation of the three-way connector 32 communicating the ventricular phantom 18 and the coronary artery phantoms 26; and the three-way connector 32 is provided with a drain valve 31 for cleaning the contrast agent remained in the phantoms; and the bottom of the water tank 29 is supported with two parallel brackets 27 to ensure the water tank 29 is at a horizontal position.

Figure 20:
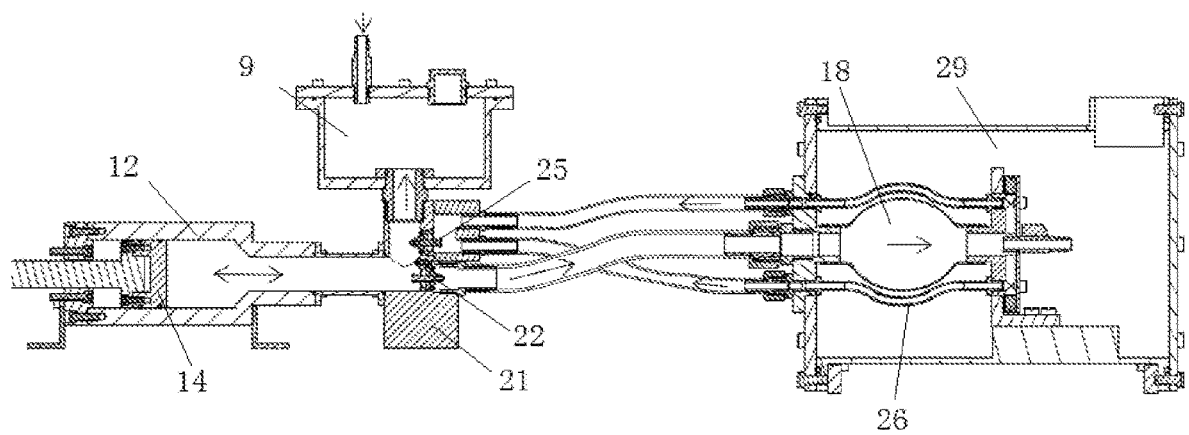
FIG. 20 is a schematic diagram of a fluid circuit according to the invention.

As shown in FIG. 20, the working principle of the fluid circuit of the system is illustrated by taking two coronary artery phantoms 26 as an example.

When the piston pump unit 6 presses out the liquid, the pump-in check valve 22 is opened, and the pump-out check valve 25 is closed; the liquid enters the ventricular phantom 18 and the two coronary artery phantoms 26 through the fluid flow sensor 20 and the pump-in pipe tube interface 23; the ventricular phantom 18 is increased in volume due to filling. This process is used to simulate a ventricular diastolic phase.

When the piston pump unit 6 draws the liquid back, the pump-in check valve 22 is closed, and the pump-out check valve 25 is opened; the liquid enters the piston pump unit 6 through the fluid flow sensor 20 via the two coronary artery phantoms 26 and the two pump-out pipe interfaces 24 from the ventricular phantom 18; and the ventricular phantom 18 is decreased in volume due to systole. This process is sued to simulate a ventricular ejection phase.

When the system is initialized, the ventricular ejection process may be used to vent the air in the fluid circuit into the atmosphere through the buffer 9; if t, there are still air existing in the fluid circuit after the venting is completed, air may also converge towards a compressed air area at the top of the buffer under the influence of the pressure of the fluid circuit in this process.

As described above, the piston pump unit 6 reciprocates according to a preset frequency and volume changes, so that the cardiovascular phantom 11 simulates the ventricular systolic-diastolic motion during the cardiac cycle.

(2) Method for Controlling the Phantom:

The method for controlling a dynamic test phantom simulating cardiovascular motion for quality evaluation of CT imaging according to the invention employs the dynamic test phantom simulating cardiovascular motion for quality evaluation of CT imaging as described in the invention, and the method includes the following steps:

acquiring ventricular motion parameters, converting the ventricular motion parameters into motion control variables, and storing the motion control variables, by a control PC 2, wherein the ventricular motion parameters include a heart rate and a ventricular volume-time curve, the motion control variables include a motion cycle, each motion phase and its flow value; when starting control, sending a start-up instruction to the PLC control system, and displaying and storing an ECG waveforms, the ventricular volume-time curve, the heart rate, a cardiac cycle, and a stroke volume in real time;

receiving a command sent from the control PC 2 by the PLC control system; if the command is the start-up instruction, parsing the motion control variables in the start-up instruction, calculating the flow of the piston pump unit in unit time using a closed-loop control algorithm, calculating motion control parameters based on displacements feedback in real time to send a motion control signal to the electric cylinder drive unit 5 while sending an ECG control command to the ECG generator to output ECG waveforms, and after waiting for the action to be completed, sending a stop instruction to the electric cylinder unit 3 and the ECG generator respectively; and if the command is a stop instruction, directly sending a stop instruction to the electric cylinder unit 3 and the ECG generator after waiting for the current action to be completed, and automatically returning to zero; then, continuing to monitor if a command from the control PC is received; and repeating the process above again and again till the end of a run.

In this embodiment, the method for controlling the dynamic test phantom simulating cardiovascular motion for quality evaluation of CT imaging includes the following steps.

Figure 21:
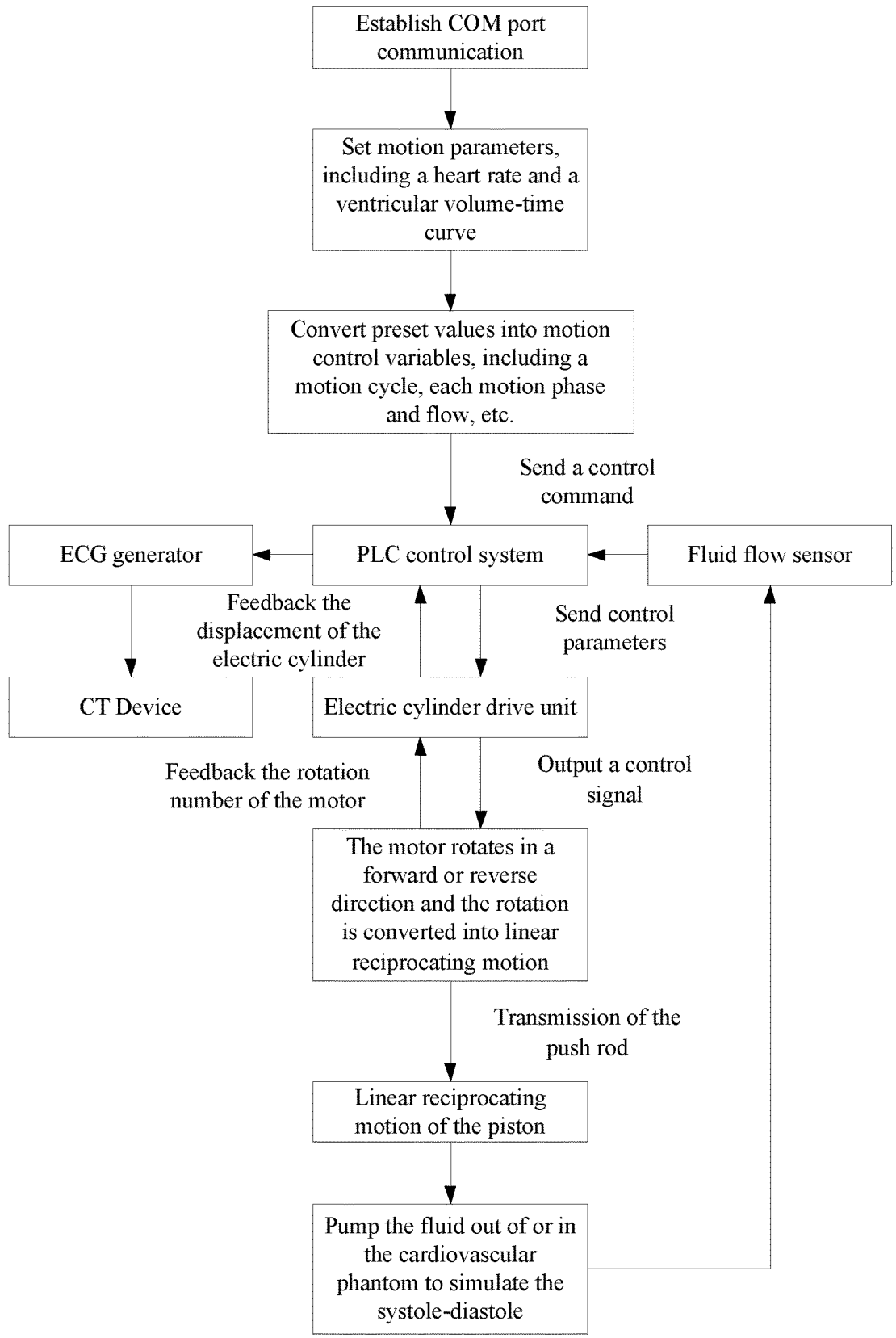
FIG. 21 is a first flowchart of a control method according to the invention.

Before the system starts control, the power of the control box 1 and the switch of the control PC 2 (for example, a computer) are turned on at first, and the computer starts and then runs the application software, which is initialized, as shown in FIG. 21.

In Step 1, a corresponding COM port number is selected to establish a COM port communication, and the control PC 2 and the PCL control system are connected;

In Step 2, a user sets the ventricular motion parameters including the heart rate and the ventricular volume-time curve according to needs, wherein the heart rate may be selected from a single heart rate, a combined heart rate or a custom heart rate sequence, and the ventricular volume-time curve corresponds to the setting of the heart rate.

In Step 3, the system automatically converts the preset values into motion control variables, including a motion cycle, each motion phase and its flow values, and stores them.

In Step 4, to start the control, the application software sends a start control command to the PLC control system, and displays and stores ECG waveforms, the ventricular volume-time curves, the heart rates, the cardiac cycles and the stroke outputs in real time; and here, the PLC control system executes the motion control command in cycles.

In Step 5, after the motion is completed, the user may send a stop control command to the PLC control system through the application software, to stop the motion of the phantom and save the relevant data.

Figure 22:
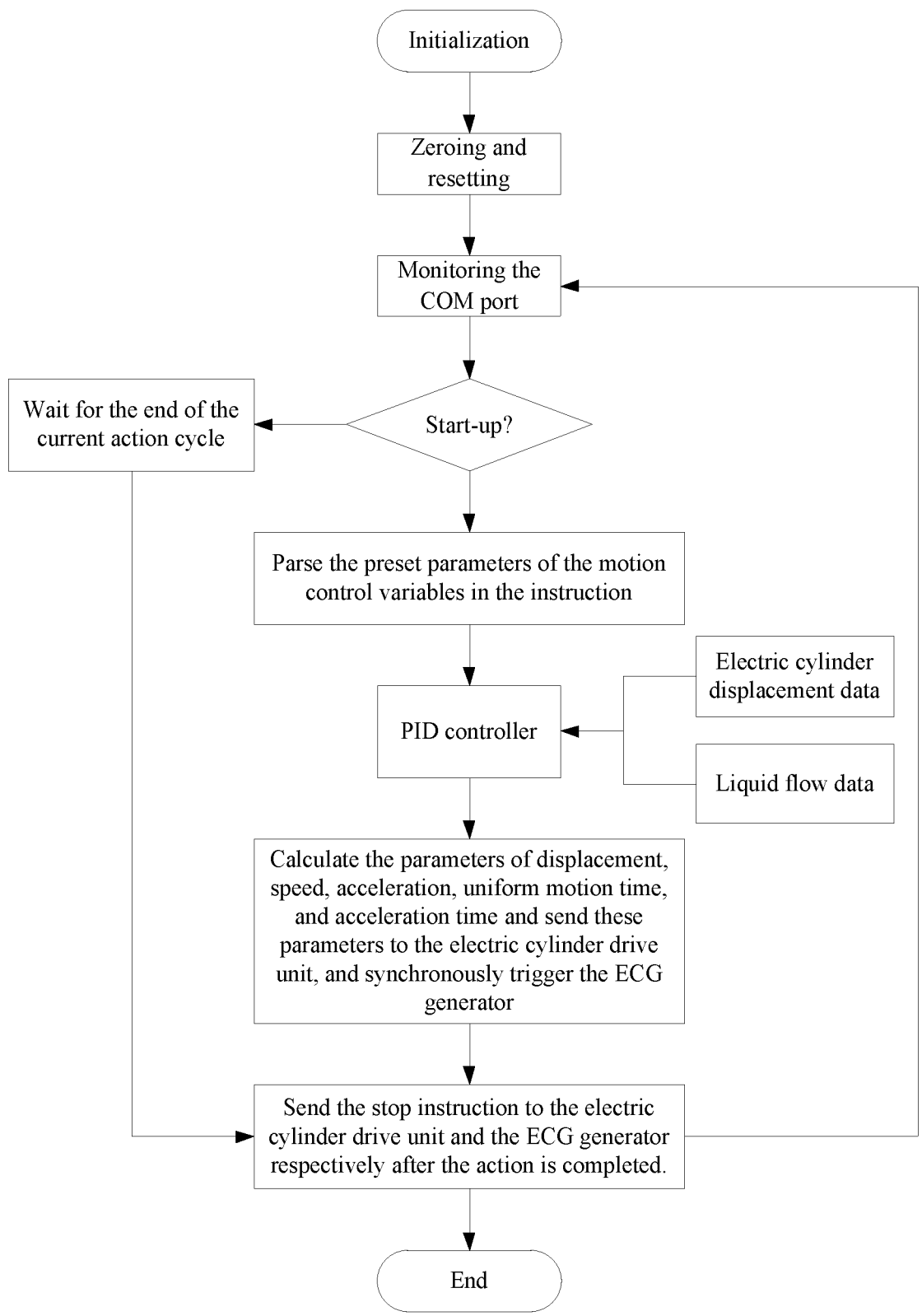
FIG. 22 is a second flowchart of a control method according to the invention.

As shown in FIG. 22, after the PLC system is powered on, the control software performs the following: first executing initializations including system parameters, electric cylinder zeroing and ECG resetting; then, monitoring in real time if a COM port receives a command from the application; if the command is the start-up instruction, parsing the motion control variables in the start-up instruction, calculating the flow of the piston pump unit in unit time using a closed-loop control algorithm (for example, a PID controller), calculating motion control parameters (for example, speed, acceleration, uniform motion time, and acceleration time) based on displacements fed back in real time, to send a motion control signal to the electric cylinder drive unit 5 while sending an ECG control command to the ECG generator to output ECG waveforms (for the first startup, the position of the electric cylinder takes a zero position as an initial position, and the ECG generator takes a P-wave as a starting point), and after waiting for the action to be completed, sending a stop instruction to the electric cylinder unit 3 and the ECG generator respectively; and if the command is a stop instruction, directly sending a stop instruction to the electric cylinder unit 3 and the ECG generator after waiting for the current action to be completed, and automatically returning to zero; then, continuing to monitor if a command from the control PC is received by the COM port; and repeating the process above again and again till the end of a run.

The following describes a conversion relationship between the ventricular motion parameters and the electric cylinder motion parameters.

Given the heart rate is 75 times/min, the cardiac cycle is 0.8 s, the sectional area of the piston 14 is 2826 mm², and the motor acceleration is constant a (mm/s²);

Suppose that the ventricle has six motion time phases including an isovolumetric systolic phase of 0.05 s, a rapid ejection phase of 0.1 s, a slow ejection phase of 0.15 s, an isovolumic diastolic phase of 0.07 s, a rapid filling phase of 0.11 s, and a slow filling phase of 0.22 s throughout the cardiac cycle, and according to the ventricular volume-time curve, each motion phase may correspond to a volume $V_{volume}$ (mm³) and a time $T_{phase}$ (s);

In one motion time phase, the actions of the electric cylinder unit 3 includes an acceleration motion, a uniform motion and a deceleration motion, that is, the following motion control parameters need to be input for the electric cylinder unit 3, including a motion speed v, an acceleration a, a uniform motion time $T_1$, and an acceleration time $T_2$. According to the given conditions above, it follows that the displacement $S_{stroke}$ of the electric cylinder unit 3 is:

$$S_{stroke} = V_{volume}/2826 \text{ mm}^2 \quad \text{Formula 1}$$

the motion speed v is:

$$V = \frac{-T_{phase} - \sqrt{T_{phase}^2 - \frac{4S_{stroke}}{a}}}{-\frac{2}{a}} \quad \text{Formula 2}$$

the uniform motion time $T_1$ and the acceleration time $T_2$ are:

$$T_2 = v/a \quad \text{Formula 3}$$

$$T_1 = T_{phase} - 2 \cdot T_2 \quad \text{Formula 4}$$

In addition, given the pitch D (mm) of the ball screw, the electric cylinder unit 3 moves for D after every turn of the motor, and it follows that Motor Speed:

$$n = v \cdot 60 \cdot 1000/D \quad \text{Formula 5}$$

Among them, the unit of n is rpm (revolution per minute).

(3) Quality Testing Method:

The CT imaging quality testing method according to the invention employs the dynamic test phantom simulating cardiovascular motion for quality evaluation of CT imaging as described in the invention, and the method includes the following steps:

Step 1, establishment of a connection, to be specific, placing the control system, the electric cylinder unit 3, the piston pump unit 6, the fluid circuit unit and the cardiovascular phantom 11 (including a coronary artery stenosis phantom 26) on a scanning bed of a CT device, and performing installation and connection;

Step 2, establishment of a fluid circuit, to be specific, first mixing distilled water and a contrast agent at certain ratio to act as a target solution, opening the water injection valve 17 and the vent hole 16 of the buffer 9, injecting the target solution into the piston pump unit 6 and the ventricular phantom 18 using a measuring cylinder, removing large air manually, closing the water injection valve 17 once completing the injection (where the liquid level shall be below the maximum scale of the buffer 9), installing the gas pressure gauge to the vent hole 16 and tightening, and then injecting the distilled water into the water tank 29 till the root of its window 30 to act as a background solution;

Step 3, power-on for startup, to be specific, turning on the power switch of the control box 1, and starting the control PC 2 (for example, a computer), where after about 1 min, the computer, the PCL control system and the electric cylinder unit 3 are powered on completely;

Step 4, removal of air, to be specific, opening the application software of the control PC 2, selecting "ventricular volume-time curve" as a default at the heart rate of 20 beats/min by way of an example, starting a motion, running till the air in the fluid circuit are removed and air at the top of the buffer 9 is compressed and then maintained at a preset pressure value, and stopping the motion after 3-5 min; or else, checking the tightness of each pipeline and its interface, and repeating the process above;

Step 5, starting of control, to be specific, setting the motion parameters (including normal heart rate, ventricular premature beat, slow atrial fibrillation, etc.) according to needs, selecting a "Start Control" button to control the piston pump to reciprocate linearly to pump a liquid out of or in the cardiovascular phantom 11 for simulating ventricular strokes and multiple motion phases, and simultaneously sending an ECG signal to trigger ECG-gated scanning of the CT device;

Step 6, image acquisition, to be specific, positioning the phantom, creating a new patient, selecting a CTA examination protocol, setting scanning conditions, and scanning the cardiovascular phantom; and Step 7, clinical evaluation, to be specific, performing post-processing and 3D reconstruction using clinical application software (for example, the Syngo Via workstation from German SIEMENS) of the CT device to obtain relevant evaluation indexes (for example, the success rate of arrhythmia image, the level of coronary artery stenosis, the quality rating of morphological image, the CT values of water and calcification, etc.) of the cardiovascular phantom 11, and evaluating the imaging quality of the CT device; and Step 8, cleaning of the fluid circuit, to be specific, sending the stop motion command by the application software; draining the background solution in the water tank 29 at first after the system stops the motion, and then opening the drain valve 31 of the piston pump unit 6 to drain the target solution; after the drainage is completed, opening the water injection valve 17 of the buffer 9 and the drain valve 31 inside the water tank 29, to wash the whole fluid circuit with the distilled water or deionized water; and after the washing is completed, disassembling the phantoms to complete the detection.

What is claimed is:

1. A dynamic test phantom simulating cardiovascular motion for quality evaluation of CT imaging, comprising: a control system, an electric cylinder unit (3), a piston pump unit (6), a fluid circuit unit and a cardiovascular phantom (11), wherein
    the control system comprises a control box (1) and a control PC (2), wherein the control box (1) comprises a PLC control system and an electrocardiogram (ECG) generator, and the PLC control system is electrically connected with the control PC (2) and the ECG generator respectively;
    the electric cylinder unit (3) comprises an electric cylinder drive unit (5) and an electric cylinder transmission unit (4), wherein the electric cylinder drive unit (5) is connected with the PLC control system and the electric cylinder transmission unit (4) respectively;
    the piston pump unit (6) is connected with the electric cylinder transmission unit (4), and the electric cylinder unit (3) controls the piston pump unit (6) to linearly reciprocate based on a command issued by the PLC control system, to pump a liquid in or out of the cardiovascular phantom (11) through the fluid circuit unit;
    the cardiovascular phantom (11) comprises a water tank (29), a ventricular phantom (18) and coronary artery phantoms (26), wherein the ventricular phantom (18) and the coronary artery phantoms (26) are disposed in the water tank (29), the water tank (29) is filled with the liquid, and the coronary artery phantoms (26) comprises a plurality of catheters, each of the plurality of catheters is in communication with the ventricular phantom (18) respectively; and
    the fluid circuit unit comprises a fluid confluence module (8) and fluid pipelines (10), wherein the fluid pipelines (10) comprise a pump-in fluid pipeline and pump-out fluid pipelines; the fluid confluence module (8) comprises a fluid flow sensor (20) and a diverter block (21); the fluid flow sensor is electrically connected with the PLC control system and is installed between the piston pump unit (6) and the diverter block (21); the diverter block (21) is internally provided with a pump-in check valve (22) and a pump-out check valve (25); the pump-in check valve (22) has a water inlet end in communication with the fluid flow sensor (20) and has a water outlet end in communication with the ventricular phantom (18) through the pump-in fluid pipeline; the pump-out check valve (25) has a water outlet end in communication with the fluid flow sensor (20) and has a water inlet end respectively in communication with one end of each of the pump-out fluid pipelines; and the other ends of the plurality of pump-out fluid pipelines are in one-to-one correspondence with the plurality of catheters respectively.

2. The dynamic test phantom simulating cardiovascular motion for quality evaluation of CT imaging according to claim 1, wherein the fluid circuit unit further comprises a buffer (9), a bottom of the buffer (9) is in communication with a top of the diverter block (21) through a buffer interface (19), and a top of the buffer (9) is provided with a water injection valve (17), a gas pressure gauge and a vent hole (16).

3. The dynamic test phantom simulating cardiovascular motion for quality evaluation of CT imaging according to claim 2, wherein the ventricular phantom (18) is made of silica gel, and has an elliptical shape with openings at both ends.

4. The dynamic test phantom simulating cardiovascular motion for quality evaluation of CT imaging according to claim 2, wherein the coronary artery phantoms (26) are synthesized from a high polymer material of a polytetrahydrofuran ether polyol-toluene diisocyanate copolymer, with a CT value ranging from 30HU-80HU.

5. The dynamic test phantom simulating cardiovascular motion for quality evaluation of CT imaging according to claim 4, wherein the coronary artery phantoms (26) are classified into a normal coronary artery phantom and a coronary artery phantom having different levels of stenosis; each catheter of the normal coronary artery phantom has the same inner diameter; and each catheter of the coronary artery phantom having different levels of stenosis has simulated calcified plaques or soft plaques in the lumen to lead to the stenosis levels of 25%, 50% and 75%.

6. The dynamic test phantom simulating cardiovascular motion for quality evaluation of CT imaging according to claim 2, wherein the PLC control system comprises a CPU module, a motion control module, two communication modules, and a power module; the CPU module is connected with the motion control module, two communication modules and the power module respectively; the motion control module is connected with the electric cylinder unit (3); one of the communication modules is connected with the control PC (2); and the other communication module is connected with the ECG generator.

7. The dynamic test phantom simulating cardiovascular motion for quality evaluation of CT imaging according to claim 6, wherein the electric cylinder transmission unit (4) comprises a motor and a transmission construct which converts the rotation of the motor into a linear motion;
    the transmission construct comprises a synchronous belt, a synchronous wheel, a ball screw, a screw nut, a cylinder body and a push rod; the motor is connected with the ball screw through the synchronous belt and the synchronous wheel; the screw nut is connected with the push rod; the push rod is located in the cylinder body; the motor is transmitted to the ball screw through the synchronous wheel and the synchronous belt; and the ball screw drives the screw nut to convert the rotation into the linear motion, so that the push rod reciprocates linearly along the cylinder body.

8. The dynamic test phantom simulating cardiovascular motion for quality evaluation of CT imaging according to claim 2, wherein the water inlet end of the ventricular phantom (18) is connected with the pump-in fluid pipeline through a pump-in pipe interface (23); and the water outlet end of the ventricular phantom (18) is in communication with each of the catheters of the coronary artery phantom (26) through a three-way connector (32), which is provided with a drain valve (31).

9. A method for controlling a test phantom simulating cardiovascular motion for quality evaluation of CT imaging, wherein the dynamic test phantom simulating cardiovascular motion for quality evaluation of CT imaging according to claim 1 is used, and the method comprises the following steps:

acquiring ventricular motion parameters, converting the ventricular motion parameters into motion control variables and storing the motion control variables, by the control PC (2), wherein the ventricular motion parameters comprise a heart rate and a ventricular volume-time curve, the motion control variables comprise a motion cycle, each motion phase and a flow value thereof; when starting control, sending a start-up instruction to the PLC control system, and displaying and storing an ECG waveform, the ventricular volume-time curve, the heart rate, a cardiac cycle, and a stroke volume in real time;

receiving a command sent from the control PC (2) by the PLC control system; if the command is the start-up instruction, parsing the motion control variables in the start-up instruction, calculating the flow of the piston pump unit in unit time using a closed-loop control algorithm, calculating motion control parameters based on displacements fed back in real time to send a motion control signal to the electric cylinder drive unit (5) while sending an ECG control command to the ECG generator to output the ECG waveform, and after waiting for the action to be completed, sending a stop instruction to the electric cylinder unit (3) and the ECG generator respectively; and if the command is a stop instruction, directly sending the stop instruction to the electric cylinder unit (3) and the ECG generator after waiting for the current action to be completed, and automatically returning to zero; then, continuing to monitor if a command from the control PC (2) is received; and repeating the process above again and again till the end of a run.

10. A CT imaging quality testing method, wherein the dynamic test phantom simulating cardiovascular motion for quality evaluation of CT imaging according to claim 1 is used, and the method comprises the following steps:

Step 1, establishment of a connection, to be specific, placing the control system, the electric cylinder unit (3), the piston pump unit (6), the fluid circuit unit and the cardiovascular phantom (11) on a scanning bed of a CT device, and performing installation and connection;

Step 2, establishment of a fluid circuit, to be specific, opening the water injection valve (17) and the vent hole (16) of the buffer (9), injecting a target solution prepared by mixing distilled water and a contrast agent into the piston pump unit (6) and the ventricular phantom (18), removing air, closing the water injection valve (17) after completing the injection, installing the gas pressure gauge to the vent hole (16) and tightening the interface, and then injecting the distilled water into the water tank (29) to act as a background solution;

Step 3, power-on for startup, to be specific, turning on the power switch of the control box (1), and starting the control PC (2);

Step 4, removal of air, to be specific, opening the application software of the control PC (2), setting the heart rate and the ventricular volume-time curve, starting a motion, running till air in the fluid circuit are removed and air at the top of the buffer (9) is compressed and then maintained at a preset pressure value, and stopping the motion; or else, checking the tightness of each pipeline and an interface thereof, and repeating the process above;

Step 5, starting of control, to be specific, setting the motion parameters through the application software of the control PC (2), sending a motion control command to the PLC control system, which controls the piston pump unit (6) to reciprocate linearly to pump a liquid out of or in the cardiovascular phantom (11) for simulating ventricular strokes and multiple motion phases, and simultaneously sending an ECG signal to trigger ECG-gated scanning of the CT device;

Step 6, image acquisition, to be specific, positioning the cardiovascular phantom (11), creating a new patient, selecting a CTA examination protocol, setting scanning conditions, and scanning the cardiovascular phantom; and Step 7, clinical evaluation, to be specific, performing post-processing and 3D reconstruction using clinical application software of the CT device to obtain relevant evaluation indexes of the cardiovascular phantom (11), and evaluating imaging quality of the CT device.

* * * * *